United States Patent
Mudya et al.

(10) Patent No.: US 11,590,064 B2
(45) Date of Patent: Feb. 28, 2023

(54) SPRAYABLE SUNSCREEN COMPOSITION

(71) Applicant: Johnson & Johnson Consumer Inc., Skillman, NJ (US)

(72) Inventors: Navya Mudya, Hillsborough, NJ (US); Frank C. Sun, Belle Mead, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 16/593,035

(22) Filed: Oct. 4, 2019

(65) Prior Publication Data

US 2021/0100726 A1   Apr. 8, 2021

(51) Int. Cl.
| | |
|---|---|
| *A61K 8/34* | (2006.01) |
| *A61K 8/37* | (2006.01) |
| *A61K 8/81* | (2006.01) |
| *A61K 8/85* | (2006.01) |
| *A61K 8/86* | (2006.01) |
| *A61Q 17/04* | (2006.01) |

(52) U.S. Cl.
CPC ............ *A61K 8/347* (2013.01); *A61K 8/37* (2013.01); *A61K 8/8152* (2013.01); *A61K 8/8158* (2013.01); *A61K 8/85* (2013.01); *A61K 8/86* (2013.01); *A61Q 17/04* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 5,204,090 A * | 4/1993 | Han .................. | A61K 8/37 424/47 |
| 6,395,269 B1 | 5/2002 | Fuller et al. | |
| 7,108,860 B2 | 9/2006 | Dueva et al. | |
| 8,557,227 B2 | 10/2013 | Simonnet et al. | |
| 8,652,449 B1 * | 2/2014 | Halpern ............... | A61K 8/35 424/60 |
| 9,144,535 B1 | 9/2015 | Daly et al. | |
| 9,144,536 B1 | 9/2015 | Daly et al. | |
| 9,149,664 B2 | 10/2015 | Davis et al. | |
| 10,092,494 B2 | 10/2018 | SaNogueira et al. | |
| 2008/0181858 A1 * | 7/2008 | Davis ................. | A61K 8/73 424/59 |
| 2009/0246165 A1 * | 10/2009 | Toreki .............. | A61P 31/00 424/78.07 |
| 2011/0171148 A1 * | 7/2011 | Jones ................ | A61Q 17/04 424/59 |
| 2013/0045254 A1 * | 2/2013 | Ting-Jenulis ........ | A61K 8/891 424/401 |
| 2017/0189294 A1 * | 7/2017 | Spaulding .............. | A61K 8/31 |
| 2017/0312199 A1 | 11/2017 | Shah et al. | |
| 2018/0263866 A1 * | 9/2018 | Deckner ............... | A61K 8/25 |
| 2019/0021967 A1 * | 1/2019 | He ......................... | A61K 8/37 |
| 2019/0374454 A1 * | 12/2019 | Johncock .............. | A61K 9/12 |

FOREIGN PATENT DOCUMENTS

| | | |
|---|---|---|
| WO | WO 2008/117017 A | 10/2008 |
| WO | WO-2016166220 A1 * | 10/2016 .............. A61P 17/02 |

OTHER PUBLICATIONS

Surface Sun Systems Wetskin Formula at dailymed.nlm.nih.gov/dailymed/fda/fdaDrugXsl.cfm?setid=6ccc1c4f-906f-17d1-e053-2991aa0a4c6a&type=display (Year: 2018).*
Agilent Technical Review (Polymer Molecular Weight Distribution and Definitions of MW Averages (Year: 2015).*
Ahmad Resonance Jan. 1998:67-72 (Year: 1998).*
Shaath, "SPF Boosters & Photostability of Ultraviolet filters", Happi (Oct. 2007) www.Happi.com, pp. 77-83.
Database GNPD [Online] MINTEL; Sep. 3, 2012 (Sep. 3, 2012). anonymous: 11 Wet Skin Continuous Spray Sunscreen SPF 7011-XP055775378. Database accession No. 1869290 * abstract *.
Database GNPD [Online] 1-7 MINTEL; Jun. 12, 2012 (Jun. 12, 2012). anonymous: 11 Continuous Mist Sunscreen for Kids SPF 7011-XP055775382. Database accession No. 1799252 * abstract *.
Database GNPD [Online] MINTEL; Apr. 15, 2013 (Apr. 15, 2013). anonymous: 11 Wet Skin Spray SPF 5011-XP055775383. Database accession No. 2039156 * abstract *.
Database GNPD [Online] MINTEL; Apr. 25, 2018 (Apr. 25, 2018). anonymous: 11 Wet Skin Kids Sunscreen Continuous Spray SPF 7011-XP055775386. Database accession No. 5624293 * abstract *.
European Search Report dated Feb. 24, 2021 for EP20199862.

* cited by examiner

*Primary Examiner* — Robert A Wax
*Assistant Examiner* — Caralynne E Helm

(57) ABSTRACT

The present invention provides an anhydrous, sprayable sunscreen composition comprising one or more oil soluble UV filters and a combination of film formers comprising at least one copolymer of trimethylolpropane, adipic acid, neopentyl glycol and hexanediol and at least one acrylates/octylacrylamide copolymer having a molecular weight of at least 50 kDA measured using Dynamic Light Scattering.

5 Claims, No Drawings

SPRAYABLE SUNSCREEN COMPOSITION

BACKGROUND OF THE INVENTION

It is well known that prolonged exposure to ultraviolet (UV) radiation, especially from the sun, can lead to the formation of light dermatoses and erythemas, and increase the risk of skin cancers, such as melanoma. Exposure to UV radiation also accelerates skin aging, such as loss of skin elasticity and wrinkling. For these reasons, sunscreen compositions are commonly used to provide photoprotection from the sun. Sprayable sunscreen compositions are a popular product form due to their convenient application.

Recently, the use of oxybenzone as a UV filter in sunscreen compositions has come under scrutiny, and there is a growing desire by consumers for oxybenzone-free sunscreens. However, removal of oxybenzone from a sunscreen formulation presents a challenge in maintaining an acceptable SPF.

Film formers are typically used in sunscreen compositions to provide more uniform distribution of the UV filters in the composition and spreading of the composition on skin, thereby increasing efficacy and SPF. A wide variety of film formers are available and used in commercial sunscreen compositions, including polyesters and acrylate copolymers. For example, U.S. Pat. No. 9,149,664 relates to sunscreen compositions comprising one or more sunscreen agents, one or more film forming polymers, and heat-treated xanthan gum. The patent discloses a long list of synthetic, water dispersible film forming polymers that may be used, including DERMACRYL 79, an acrylates/octylacrylamide copolymer, LEXFILM SUN, polyester-7, a copolymer of trimethylolpropane, adipic acid, neopentyl glycol and hexanediol (and) neopentyl glycol diheptanoate, and LEXFILM SPRAY, polyester-10, a copolymer of hexanediol, neopentyl glycol, adipic acid and pyromellitic dianhydride (and) propylene glycol dibenzoate. Use of a specific combination of film formers comprising the specific combination of at least one copolymer of trimethylolpropane, adipic acid, neopentyl glycol and hexanediol and at least one acrylates/octylacrylamide copolymer is not, however, taught or suggested.

It has now been discovered that a sprayable, anhydrous sunscreen composition that may additionally be substantially or completely free of oxybenzone while providing a surprisingly high SPF may be prepared using a combination of film formers comprising at least one copolymer of trimethylolpropane, adipic acid, neopentyl glycol and hexanediol and at least one acrylates/octylacrylamide copolymer having a molecular weight of at least 50 kDA measured using Dynamic Light Scattering.

SUMMARY OF THE INVENTION

The present invention provides a sunscreen composition comprising one or more oil soluble UV filters and a combination of film formers comprising at least one copolymer of trimethylolpropane, adipic acid, neopentyl glycol and hexanediol and at least one acrylates/octylacrylamide copolymer having a molecular weight of at least 50 kDA measured using Dynamic Light Scattering, wherein the composition is anhydrous and sprayable.

DETAILED DESCRIPTION OF THE INVENTION

Unless defined otherwise, all technical and scientific terms used herein have the same meaning as commonly understood by one of ordinary skill in the art to which the invention belongs. All publications, patent applications, patents, and other references mentioned herein are incorporated by reference.

Where applicable, chemicals are specified according to their INCI Name. Additional information, including definitions, suppliers, and trade names, can be found under the appropriate INCI monograph in the International Cosmetic Ingredient Dictionary and Handbook, 16th Edition published by the Personal Care Products Council, Washington D.C. Also available via the Personal Care Products Council On-Line INFOBASE (online.personalcarecouncil.org/jsp/Home.jsp).

As used herein, "topically applying" means directly spraying, wiping, laying on, or spreading on outer skin or the scalp, e.g., by use of the hands or an applicator such as a wipe, roller, or spray.

As used herein, "cosmetic" refers to a beautifying substance or preparation which preserves, restores, bestows, simulates, or enhances the appearance of bodily beauty or appears to enhance the beauty or youthfulness, specifically as it relates to the appearance of tissue or skin.

As used herein, "sunscreen composition" refers to a formulation (e.g. a lotion, spray, gel or other topical product) that absorbs and/or reflects some of the sun's ultraviolet (UV) radiation and thus helps protect against negative effects of sun exposure, e.g. sunburn, premature aging, etc.

As used herein, "cosmetically effective amount" means an amount of a physiologically active compound or composition sufficient for treating one or more conditions, but low enough to avoid serious side effects. The cosmetically effective amount of the compound or composition will vary with the condition being treated, the age and physical condition of the end user, the severity of the condition being treated/prevented, the duration of the treatment, the nature of other treatments, the specific compound or product/composition employed, the cosmetically-acceptable carrier utilized, and like factors.

As used herein, "cosmetically acceptable" means that the ingredients the term describes are suitable for use in contact with tissues (e.g., the skin) without undue toxicity, incompatibility, instability, irritation, allergic response, or the like.

As used herein, a "cosmetically acceptable active agent" is a compound (synthetic or natural) that has a cosmetic or therapeutic effect on the skin.

As used herein, "treatment or treating" refers to mitigating, reducing, preventing, improving, or eliminating the presence or signs of a condition or disorder.

"Phase stability" as used herein means the maintenance of interfacial stability or suspension stability or both at each of the temperatures 25° C., 40° C., and 50° C. for at least 2 weeks. "Interfacial stability" refers to stability against coalescence and coarsening of a discontinuous phase in a composition having two or more phases. "Suspension stability" refers to stability against creaming and/or sedimentation of a discontinuous phase, for example solids, suspended in continuous phase.

As used herein, "substantially free of" means the ingredient referred to is not directly and intentionally added to the formula. Preferably, "substantially free of" means containing less than about 1% of an ingredient. More preferably "substantially free of" means containing less than about 0.5% of an ingredient. Even more preferably "substantially free of" means containing less than about 0.1% by weight of an ingredient. The composition may be completely free of an ingredient, i.e., contain none of the ingredient.

Unless otherwise indicated, a percentage or concentration refers to a percentage or concentration by weight (i.e., % (W/W)). Unless stated otherwise, all ranges are inclusive of the endpoints, e.g., "from 4 to 9" includes the endpoints 4 and 9.

UV Filter

The composition comprises one or more oil soluble UV filters.

As used herein, "organic UV filter" means an organic molecule capable of absorbing UV light, including: (i) aromatic compound conjugated with a carbonyl moiety substituted in the ortho- or para-position of the aromatic ring, and (ii) polymers made of organic chromophores attached to a polymer chain, either of which block or absorb ultraviolet (UV) light.

Traditional organic UV filters are aromatic, small molecules with molecular weight values <900 g/mol. Examples of organic non-polymeric UV filters include, but are not limited to: methoxycinnamate derivatives such as octyl methoxycinnamate and isoamyl methoxycinnamate; camphor derivatives such as 4-methyl benzylidene camphor, camphor benzalkonium methosulfate, and terephthalylidene dicamphor sulfonic acid; salicylate derivatives such as octyl salicylate, ethylhexyl salicylate and homosalate; benzone derivatives such as dioxybenzone, and oxybenzone; benzoic acid derivatives such as aminobenzoic acid and octyldimethyl para-amino benzoic acid; octocrylene and other β,β-diphenylacrylates; dioctyl butamido triazone; octyl triazone; avobenzone (butyl methoxydibenzoylmethane); menthyl anthranilate; triazone derivatives such as ethylhexyl triazone (Uvinul® T150); diethylhexyl butamido triazone (UVA-Sorb® HEB); bis-ethylhexyloxyphenol methoxyphenyl triazine (Tinosorb® S), benzoate derivatives such as diethylamino hydroxybenzoyl hexyl benzoate (Uvinul® A Plus), benzotriazole derivatives such as drometrizole trisiloxane (Mexoryl® XL), methylene bis-benzotriazolyl tetramethylbutylphenol (Tinosorb® M); tris-biphenyl triazine; (2-{4-[2-(4-Diethylamino-2-hydroxy-benzoyl)-benzoyl]-piperazine-1-carbonyl}-phenyl)-(4-diethylamino-2-hydroxyphenyl)-methanone; merocyanine derivatives; bis (butylbenzoate) diaminotriazine aminopropylsiloxane; and bis-ethylhexyloxyphenol methoxyphenyl triazine, encapsulated in a polymer matrix.

Polymeric, organic UV filters are polymers made of organic chromophores attached to polymer chains, for instance a polysiloxane chain having for example an average molecular weight of >6000 Daltons. Examples of such polysiloxane UV filters include, without limitation Parsol® SLX and polysilicone-15. These polysiloxanes absorb in the UVB ($\lambda_{max}$=312 nm) part of the spectrum and are typically combined with UVA filters to achieve broad-spectrum protection.

The following table lists various commercially available organic UV filters.

| UV Filter | Other names | Coverage |
| --- | --- | --- |
| Benzophenone-3 | Oxybenzone or 2-hydroxy-4-methoxybenzophenone | UVA/B |
| Benzophenone-5 | 2-hydroxy-4-methoxybenzophenone-5-sulfonic acid (benzophenone-5) and its sodium salt<br>Sulizobenzone sodium<br>Sodium hydroxymethoxybenzophenone sulfonate | UVA/B |
| Benzophenone-8 | Dioxybenzone or 2,2'-dihydroxy-4-methoxybenzophenone dioxybenzone (2-hydroxy-4-methoxyphenyl)(2-hydroxyphenyl)methanone methanone, (2-hydroxy-4-methoxyphenyl)(2-hydroxyphenyl) | UVA/B |
| 3-benzylidene camphor | 3-benzylidene camphor | UVB |
| Bis ethylhexyloxyphenol methoxyphenyl triazine | Tinosorb S or (1,3,5)-triazine-2,4-bis {[4-(2-ethyl-hexyloxy)-2-hydroxy]-pheny}-6-(4-methoxyphenyl) or anisotriazine | UVA/B |
| Butylmethoxy dibenzoyl methane | Avobenzone or 1-(4-tert-butylphenyl)-3-(4-methoxyphenyl) propane-1,3-dione | UVA |
| Camphor benzalkonium Methosulfate | Mexoryl SO or N,N,N-trimethyl-4-(2-oxoborn-3-ylidene-methyl) anilinium methyl sulphate | UVB |
| Diethylamino hydroxybenzoyl hexyl benzoate | Uvinul A plus or benzoic acid, 2-[-4-(diethylamino)-2-hydroxybenzoyl]-, hexylester | UVA |
| Diethylhexyl butamido triazone | UVASorb HEB or benzoic acid, 4,4-((6-((4-(((1,1-dimethylethyl) amino) carbonyl) phenyl) amino) 1,3,5-triazine-2,4-diy1) diimino) bis-(2-) ester) or dioctyl butamido triazone | UVB |
| Drometrizole trisiloxane | Mexoryl XL or phenol,2-(2H-benzotriazol-2-yl)-4-methyl-6-(2-methyl-3-(1,3,3,3-tetramethyl-1-(trimethylsilyl)oxy)-disiloxanyl)propyl) | UVA/B |
| Ethoxyethyl methoxycinnamate | Cinoxate | UVB |
| Ethylhexyl dimethylamino Benzoate | Padimate O<br>Octyl dimethyl PABA<br>Ethylhexyl dimethyl PABA | UVB |
| Ethylhexyl methoxycinnamate | OMC or octinoxate<br>Octyl methoxycinnamate | UVB |

| UV Filter | Other names | Coverage |
| --- | --- | --- |
| Ethylhexyl salicylate | Octisalate<br>2-ethylhexyl salicylate<br>Octyl salicylate | UVB |
| Ethylhexyl triazone | Uvinul T150<br>2,4,6-trianilino-(p-carbo-2'-ethylhexyl-1'oxy)-1,3,5-triazine<br>Octyl triazone | UVB |
| Homosalate | 3,3,5-trimethylcyclohexyl 2-hydroxybenzoate<br>Salicilato de homomentila | UVB |
| Isoamyl p-methoxycinnamate | Amiloxate<br>Isopentyl-4-methoxycinnamate | UVB |
| Methyl anthranilate | Meradimate | UVA |
| 4-methylbenzylidene camphor | Enzacamene<br>3-(4'-methylbenxylidene)d-1 camphor<br>4 MBC | UVB |
| Methylene bis-benzotriazolyl tetramethylbutylphenol | Tinosorb M<br>2,2'-methylene-bis-6-(2H-benzotriazol-2yl)-4-(tetra methyl-butyl)-1,1,3,3-phenol | UVA/B |
| Octocrylene | 2-cyano-3,3-diphenyl acrylic acid, 2-ethylhexyl ester | UVB |
| Para aminobenzoic acid | PABA<br>4-aminobenzoic acid | UVB |
| Polyacrylamido methylbenzylidene Camphor | Mexoryl SW<br>Polymer of N-[(2 and 4)-[(2-oxoborn-3-ylidene)methyl]benzyl]acrylamide | UVB |
| Polysilicone-15 | Parsol SLX<br>Diethylbenzylidene malonate Dimethicone<br>Diethylmalonylbenzylidene Oxypropene dimethicone<br>Dimethicodiethylbenzalmalonate | UVB |
| Triethanolamine salicylate | Neo Heliopan TES<br>Trolamine salicylate | UVB |
| Terephtalydene dicamphor sulfonic acid | Mexoryl SX | UVA |

The sunscreen composition may comprise at least about 10 weight percent of one or more oil soluble UV filters based on the total weight of the composition. The composition may comprise about 15 to about 35 weight percent of one or more oil soluble UV filters based on the total weight of the composition. The composition may comprise at least about 21 weight percent of one or more oil soluble filters based on the total weight of the composition, particularly when a transparent composition is desired.

The oil soluble UV filters may be selected from one or more of homosalate, octisalate, avobenzone, octocrylene.

The oil soluble UV filters may be a mixture of homosalate, octisalate, avobenzone, octocrylene. For example, the sunscreen composition may comprise about 8 to about 15 weight percent homosalate, about 4 to about 5 weight percent octisalate, about 2 to about 3 weight percent avobenzone, and about 7 to about 10 weight percent octocrylene, based on the total weight of the composition.

The sunscreen composition may be substantially free of oxybenzone. The sunscreen composition may be completely free of oxybenzone.

The composition may optionally contain one or more UV blockers, which are compounds that reflect, absorb or scatter the UV radiation. When present in sunscreen compositions they reflect the ultraviolet, visible and infrared rays to enhance sun protection. UV blockers are typically inorganic metallic oxides, including titanium dioxide, zinc oxide, and certain other transition metal oxides. Such UV blockers are typically solid particles in a micronized or nanonized form having a diameter from about 0.01 micron to about 10 microns.

Examples include zinc oxide, titanium dioxide, doped zinc oxide, doped titanium dioxide, and other transition metal oxides. Doped metal oxides contain dopants that are trace elements of other metal atoms incorporated into the crystal lattice of the primary metal oxide to modify its electrical or optical properties and may include aluminum, manganese, and iron.

In another embodiment, the metal oxide comprises coated particles. The coating may comprise for example hydrophobic materials such as alkyl siloxanes (e.g. triethoxycaprylylsilane), silicones or metal salts of fatty acids.

In one embodiment, the metal oxide comprises particles having a diameter from about 0.01 micron to about 10 microns.

In one embodiment, the inorganic sunscreen may further comprise particulate doped zinc oxides as referred in U.S. Pat. Nos. 9,144,535, 9,144,536 and WO2008117017, incorporated herein by reference in their entirety. Such particulate zinc oxides comprise low levels of certain dopants at particular ratios and provide improved performance with respect to absorption in the UVA portion of the electromagnetic spectrum. The particulate zinc oxides comprise a cationic portion that in turn comprises about 99% by weight or more of a zinc portion. The cationic portion further comprises first and second dopant portions comprising metals such as manganese, iron, aluminum, and copper. The first and second dopant portions may be present in amounts of about 0.1% to about 0.75% by weight of the cationic portion. The particulate doped zinc oxides may further comprise additional metal cations, for example, cations of alkali metals, alkaline earth metals, other transition metals, as well as cations of metals such as gallium, germanium, gallium, indium, tin, antimony, thallium, lead, bismuth, and polonium, in small concentrations.

These doped zinc oxides may be made by various methods, such as by reducing oxide ores using, for example, carbon or other suitable reducing agents, and then re-oxidizing. Other suitable methods include wet chemical methods. One example of a wet chemical method includes mixing alkaline salt solutions of the various cations and causing ZnO to precipitate by reducing the pH using an acid such as oxalic or formic acid. A particularly suitable wet chemical method is the so-called "sol-gel" method.

SPF

Sun protection factor (SPF) may be tested using the following IN VITRO SPF TEST METHOD. The baseline transmission of a PMMA plate (substrate, available from Helioscience, Marseille, France) is measured for UV absorbance using calibrated Labsphere® UV-10005 UV transmission analyzer or a Labsphere® UV-2000S UV transmission analyzer (Labsphere, North Sutton, N.H., USA). A test sample is then applied to the PMMA plate using an application density of about 1.3 mg/cm$^2$ by rubbing into a uniform thin layer with the operator's finger. The sample is allowed to dry for 15 minutes and then measured for UV absorbance in the same way. The absorbance measures are used to calculate SPF as known in the art using the following equation:

$$SPF \text{ in vitro} = \frac{\int_{\lambda=290 \text{ nm}}^{\lambda=400 \text{ nm}} E(\lambda) * I(\lambda) * d\lambda}{\int_{\lambda=290 \text{ nm}}^{\lambda=400 \text{ nm}} E(\lambda) * I(\lambda) * 10^{A_0(\lambda)} * d\lambda}$$

in which:

$E(\lambda)$ = Erythema action spectrum;

$I(\lambda)$ = Spectral irradiance received from the UV source;

$A_0(\lambda)$ = Mean monochromatic absorbance of the test product layer before UV exposure; and $d(\lambda)$ = Wavelength step (1 nm).

In one embodiment, the composition has an SPF as measured by the IN VITRO SPF TEST METHOD of at least about 15. In another embodiment, the composition has an SPF as measured by the IN VITRO SPF TEST METHOD of at least about 25.

The composition may comprise one or more SPF boosters, such as styrene/acrylates copolymer. A commercially available styrene/acrylates copolymer is SUNSPHERES Powder from Dow Chemical.

Film Formers

Film formers are generally polymers that, when dissolved in a composition, permit a continuous or semi-continuous film to be formed when the composition is spread onto, e.g., smooth glass, and the liquid vehicle is allowed to evaporate. As such, the polymer should dry on the glass in predominantly continuous manner, rather than forming a plurality of discrete, island-like structures. Generally, the films formed by applying the sunscreen compositions on the skin according to the invention are less than, on average, about 100 microns in thickness, such as less than about 50 microns.

The sunscreen composition comprises a combination of film formers comprising at least one copolymer of trimethylolpropane, adipic acid, neopentyl glycol and hexanediol and at least one acrylates/octylacrylamide copolymer having a molecular weight of at least 50 kDA measured using Dynamic Light Scattering.

The composition may comprise a combination of film formers consisting of at least one copolymer of trimethylolpropane, adipic acid, neopentyl glycol and hexanediol and at least one acrylates/octylacrylamide copolymer having a molecular weight of at least 50 kDA measured using Dynamic Light Scattering.

The composition may comprise a combination of film formers consisting of one copolymer of trimethylolpropane, adipic acid, neopentyl glycol and hexanediol and one acrylates/octylacrylamide copolymer having a molecular weight of at least 50 kDA measured using Dynamic Light Scattering.

The total amount of film formers in the composition may range from about 0.25% to about 15% by weight of the composition based on the total weight of the composition. The total amount of film formers in the composition may range from about 0.5% to about 10% by weight of the composition based on the total weight of the composition. The total amount of film formers in the composition may range from about 1% to about 5% by weight of the composition based on the total weight of the composition by weight of the composition based on the total weight of the composition.

The weight ratio of copolymer of trimethylolpropane, adipic acid, neopentyl glycol and hexanediol to acrylates/octylacrylamide copolymer in the composition may range from about 0.50 to about 3.00.

Acrylates/Octylacrylamide Copolymer

The acrylates/octylacrylamide copolymer is a copolymer of acrylate and octylacrylamide monomers. It has a molecular weight of at least 50 kDA measured using Dynamic Light Scattering. The acrylates/octylacrylamide copolymer may have a molecular weight of at least 60 kDA measured using Dynamic Light Scattering.

The molecular weight of the acrylates/octylacrylamide copolymer is measured using Dynamic Light Scattering (DLS, also known as Photon Correlation Spectroscopy or PCS) as follows. DLS is a well-known method for estimating the z-average molecular weight of a macromolecule using its measured hydrodynamic radius, $d_r$.

Samples of a solution of the acrylates/octylacrylamide copolymer are prepared by dissolving a minimum of 0.1-0.5 wt % of the copolymer into ethanol. The samples are agitated on a vortex mixer at 1000 rpm for a minimum of five minutes and then allowed to stand overnight prior to analysis. Samples are then transferred into dust-free disposable acrylic sizing cuvettes and sealed.

The samples are analyzed using a Zetasizer Nano ZS DLS instrument (Malvern Panalytical, Inc., Westborough, Mass.) operating at 25.0° C. Samples must yield a minimum count rate of 100,000 counts per second (cps) for accurate determination of the hydrodynamic radius. For samples with count rates below this minimum, the sample concentration may be gradually increased until the minimum count rate is achieved. Values of macromolecule $d_r$ are calculated using the Zetasizer Software v7.01 package (Malvern Panalytical, Inc., Westborough, Mass.), which calculates the Z-average $d_r$. The Molecular Weight is then estimated in combination with the calibration curves within the software for mass vs size for specific macromolecular conformations. The copolymer is assumed to be linear in conformation. The calibration curves of mass vs size for linear polymers are based off Pullulans or linear polysaccharides. The output from the software is a Molecular Weight (MW) of a Linear Polymer in kilodaltons (kDA). A suitable acrylates/octylacrylamide copolymer for use in the invention is DERMACRYL 79 commercially available from Nouryon. DERMACRYL 79 has molecular weight of 65.5 kDA measured using Dynamic Light Scattering.

The amount of acrylates/octylacrylamide copolymer in the composition may range from about 0.50 to about 3.25% by weight based on the total weight of the composition.

Polyester

The copolymer of trimethylolpropane, adipic acid, neopentyl glycol and hexanediol is also known as polyester 7. The copolymer may be solubilized in a solvent. The solvent may be neopentyl glycol diheptanoate.

Examples of suitable copolymers of trimethylolpropane, adipic acid, neopentyl glycol and hexanediol, include LEXFILM SUN, commercially available from INOLEX (Philadelphia, Pa.).

The amount of copolymer of trimethylolpropane, adipic acid, neopentyl glycol and hexanediol in the composition may range from about 0.25 to about 2.5% by weight based on the total weight of the composition. The amount of copolymer of trimethylolpropane, adipic acid, neopentyl glycol and hexanediol in the composition may range from 0.35 to about 1.75% by weight based on the total weight of the composition.

Alcohol

The sunscreen composition is anhydrous. The composition may be substantially free of water. The composition may be completely free of water.

The sunscreen composition comprises one or more alcohols that may function as solvents for the other ingredients in the composition.

The alcohols may for example be selected from propylene glycol, 1,3-propanediol, butylene glycol, polyethylene glycol, polypropylene glycol, glycerol, 1,2,4-butanetriol, sorbitol esters, 1,2,6-hexanetriol, ethanol, isopropanol, and mixtures thereof.

In one embodiment, the alcohol is ethanol.

The composition may comprise about 30 to about 79 weight percent of alcohol based on the total weight of the composition. In a preferred embodiment, the composition may comprise about 50 to about 79 weight percent of alcohol based on the total weight of the composition.

Topical Composition

The composition may be prepared using mixing and blending methodology well known in the sunscreen and cosmetic art.

The composition may be combined with a "cosmetically-acceptable topical carrier," i.e., a carrier for topical use that capable of containing the other ingredients dispersed or dissolved therein, and possessing acceptable properties rendering it safe to use topically.

The cosmetically-acceptable topical carrier may optionally comprise a wide variety of additional oil-soluble materials and/or oil-dispersible materials conventionally used in compositions for use on skin, at their art-established levels. For example, surfactants, emulsifiers, pearlescent or opacifying agents, thickeners, emollients, conditioners, humectants, chelating agents, exfoliants, preservatives, pH adjusting agents, and additives that enhance the appearance, feel, or scent of the composition, such as colorants, fragrances, tactile modifiers, and the like, can be included.

The composition may optionally comprise additional film formers for instance natural polymers such as polysaccharides or proteins and synthetic polymers such as other polyesters, polyacrylics, polyurethanes, vinyl polymers, polysulfonates, polyureas, polyoxazolines, and the like. Specific examples include acrylates/dimethicone acrylate copolymer (commercially available as X-22-8247D from Shin-Etsu of Japan); hydrogenated dimer dilinoleyl/dimethylcarbonate copolymer (commercially available from BASF Corp. as COSMEDIA DC); copolymers of vinylpyrrolidone and a long-chain alpha-olefin (such as those commercially available from Ashland Specialty Ingredients as GANEX V220); vinylpyrrolidone/tricontanyl copolymers (commercially available as GANEX WP660 also from Ashland).

Suitable emollients include mineral oils, petrolatum, vegetable oils (e.g. triglycerides such as caprylic/capric triglyceride), waxes and other mixtures of fatty esters, including but not limited to esters (e.g. isopropyl palmitate, isopropyl myristate, diisopropyl adipate, dibutyl adipate, dicaprylyl carbonate, C12-15 alkyl benzoate), silicone oils such as dimethicone, and alkanes such as isohexadecane.

In one embodiment, the composition may be substantially free of silicones.

In certain embodiments, the composition includes a pigment suitable for providing color or hiding power. The pigment may be one suitable for use in a color cosmetic product, including compositions for application to the hair, nails and/or skin, especially the face. Color cosmetic compositions include, but are not limited to, foundations, concealers, primers, blush, mascara, eyeshadow, eyeliner, lipstick, nail polish and tinted moisturizers. The pigment suitable for providing color or hiding power may be composed of iron oxides, including red and yellow iron oxides, titanium dioxide, ultramarine and chromium or chromium hydroxide colors, and mixtures thereof. The pigment may be a lake pigment, e.g. an organic dye such as azo, indigoid, triphenylmethane, anthraquinone, and xanthine dyes that are designated as D&C and FD&C blues, browns, greens, oranges, reds, yellows, etc., precipitated onto inert binders such as insoluble salts. Examples of lake pigments include Red #6, Red #7, Yellow #5, Violet #2 and Blue #1. The pigment may be an interference pigment. Examples of interference pigments include those containing mica substrates, bismuth oxycloride substrates, and silica substrates, for instance mica/bismuth oxychloride/iron oxide pigments commercially available as CHROMALITE pigments (BASF), titanium dioxide and/or iron oxides coated onto mica such as commercially available FLAMENCO pigments (BASF), mica/titanium dioxide/iron oxide pigments including commercially available KTZ pigments (Kobo products), CELLINI pearl pigments (BASF), and borosilicate-containing pigments such as REFLECKS pigments (BASF).

In one embodiment, the composition comprises a humectant such as butylene glycol or glycerin. The composition may comprise for example at least about 1.0 weight percent of a humectant.

The composition may further comprise one or more other cosmetically acceptable active agents include for example anti-acne agents, shine control agents, anti-microbial agents, anti-inflammatory agents, anti-mycotic agents, anti-parasite agents, external analgesics, antioxidants, keratolytic agents, moisturizers, nutrients, vitamins, energy enhancers, anti-perspiration agents, astringents, deodorants, firming agents, anti-callous agents, and agents for skin conditioning.

The amount of other cosmetically active agents may range from about 0.001% to about 20% by weight of the composition, e.g., about 0.005% to about 10% by weight of the composition, such as about 0.01% to about 5% by weight of the composition.

The cosmetically acceptable active agent may be selected for instance from D-panthenol carotenoids, ceramides, polyunsaturated fatty acids, essential fatty acids, enzymes such as laccase, enzyme inhibitors, minerals, steroids such as hydrocortisone, 2-dimethylaminoethanol, copper salts such as copper chloride, peptides like argireline, syn-ake and those containing copper, coenzyme Q10, amino acids such as proline, vitamins, lactobionic acid, acetyl-coenzyme A, niacin, riboflavin, thiamin, ribose, electron transporters such as NADH and FADH2, natural extracts such as from aloe vera, feverfew, oatmeal, dill, blackberry, princess tree, *Picia anomala*, and chicory, resorcinols such as 4-hexyl resorcinol, curcuminoids, sugar amines such as N-acetyl glucosamines, and derivatives and mixtures thereof.

Examples of vitamins include, but are not limited to, vitamin A, vitamin B's such as vitamin B3, vitamin B5, and vitamin B12, vitamin C, vitamin K, and different forms of vitamin E like alpha, beta, gamma or delta tocopherols or their mixtures, and derivatives thereof.

Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but are not limited to, extracts containing flavonoids and isoflavonoids and their derivatives (e.g., genistein and diadzein), extracts containing resveratrol and the like. Examples of such natural extracts include grape seed, green tea, pine bark, and propolis.

Sprayability

The composition of the invention is sprayable. "Sprayable" as used herein means the composition, when manually actuated or through pressurized release out of a dispensing mechanism, such as a bottle with pump spray nozzle or an aerosol can, creates a spray pattern evenly distributed and reproducible over an area of a defined shape (e.g. circle, annulus) and size. The composition may be sprayable without the use of propellants, i.e., in non-aerosol form.

The following non-limiting example further illustrate the invention.

Example

The following Compositions 1-5 according to the invention and comparative Compositions A-D were made using the ingredients shown in the following Table 1.

TABLE 1

| INCI | Function | Weight (%) |
| --- | --- | --- |
| Homosalate | Sunscreen Agent | 10.00 |
| Octisalate | Sunscreen Agent | 5.00 |
| Avobenzone | Sunscreen Agent | 3.00 |
| Octocrylene | Sunscreen Agent | 10.00 |
| Tocopheryl Acetate | Skin Conditioner | 0.10 |
| Alcohol Denat. (ethanol) | Solvent | 65.00 |
| Fragrance | Fragrance | 0.40 |
| Dicaprylyl Carbonate | Emollient | 4.50 |

In addition, each composition contained one or more of the following film formers:

(i) Polyester-7, a copolymer of trimethylolpropane, adipic acid, neopentyl glycol and hexanediol (and) neopentyl glycol diheptanoate (LEXFILM SUN), (ii) Polyester-10, a copolymer of hexanediol, neopentyl glycol, adipic acid and pyromellitic dianhydride (and) propylene glycol dibenzoate (LEXFILM SPRAY), (iii) Acrylates/octylacrylamide copolymer having a molecular weight of 65.5 kDA measured using Dynamic Light Scattering (DERMACRYL 79), (iv) Acrylates/octylacrylamide copolymer having a molecular weight of 41.1 kDA measured using Dynamic Light Scattering (AMPHOMER 4961).

The compositions were made as follows.

Homosalate, octisalate, and octocrylene were added into a main vessel and mixed at 300 rpm until uniform. While continued to mix, added dicaprylyl carbonate, polyester-7 or polyester-10 (when used) and alcohol denat. and mixed until uniform. Next added tocopheryl acetate and fragrance and continued to mix. Slowly added avobenzone and mixed until it was completely dissolved and clear. When acrylates/octylacrylamide copolymer was used, as a last step slowly sprinkled it in while continuously mixing. Continued to mix until fully dissolved and clear.

In vitro SPF was measured for each composition using the IN VITRO SPF TEST METHOD set forth above.

The results are shown in Table 2.

TABLE 2

| COMPOSITION | Film Formers | Weight % Film Former | Total Weight % Film Formers | SPF Value |
| --- | --- | --- | --- | --- |
| 1 | Dermacryl 79 | 0.70 | 2.00 | 61.05 |
|  | Lexfilm Sun | 1.30 |  |  |
| A (Comparative) | Amphomer | 0.70 | 2.00 | 28.05 |
|  | Lexfilm Sun | 1.30 |  |  |
| B (Comparative) | Dermacryl 79 | 0.70 | 2.00 | 24.48 |
|  | Lexfilm Spray | 1.30 |  |  |
| C (Comparative) | Dermacryl 79 | 2.00 | 2.00 | 28.93 |
| D (Comparative) | Lexfilm Sun | 2.00 | 2.00 | 15.28 |
| 2 | Dermacryl 79 | 0.65 | 1.00 | 44.57 |
|  | Lexfilm Sun | 0.35 |  |  |
| 3 | Dermacryl 79 | 3.25 | 5.00 | 89.17 |
|  | Lexfilm Sun | 1.75 |  |  |
| 4 | Dermacryl 79 | 1.00 | 2.00 | 50.09 |
|  | Lexfilm Sun | 1.00 |  |  |
| 5 | Dermacryl 79 | 0.50 | 2.00 | 46.73 |
|  | Lexfilm Sun | 1.50 |  |  |

Surprisingly, compositions 1-5 containing a combination of a copolymer of trimethylolpropane, adipic acid, neopentyl glycol and hexanediol and an acrylates/octylacrylamide copolymer having a molecular weight of at least 50 kDA measured using Dynamic Light Scattering as film formers exhibited SPF values of 44.57 or higher. In contrast, Compositions C and D containing only one of these film formers but not both provided SPF values of 28.93 and 15.28.

Moreover, Composition A containing a copolymer of trimethylolpropane, adipic acid, neopentyl glycol and hexanediol and an acrylates/octylacrylamide copolymer having a molecular weight of only 41.1 kDA measured using Dynamic Light Scattering (AMPHOMER 4961) provided an SPF of only 28.05.

Similarly, Composition B containing a copolymer of hexanediol, neopentyl glycol, adipic acid and pyromellitic dianhydride and an acrylates/octylacrylamide copolymer having a molecular weight of at least 50 kDA measured using Dynamic Light Scattering provided an SPF of only 24.48.

The invention claimed is:

1. A sunscreen composition comprising homosalate, octisalate, avobenzone, octocrylene, a copolymer of trimethylolpropane, adipic acid, neopentyl glycol and hexanediol, neopentyl glycol diheptanoate, and an acrylates/octylacrylamide copolymer having a molecular weight of 65.5 kDA measured using Dynamic Light Scattering;
   wherein the weight ratio of the copolymer of trimethylolpropane, adipic acid, neopentyl glycol and hexanediol to the acrylates/octylacrylamide copolymer is about 0.5 to about 3.0;
   wherein the total amount of the copolymer of trimethylolpropane, adipic acid, neopentyl glycol and hexanediol, neopentyl glycol diheptanoate, and the acrylates/octylacrylamide copolymer is about 1 weight percent to about 5 weight percent based upon the total weight of the composition;
   wherein the composition is anhydrous, sprayable, and substantially free of oxybenzone.

2. The composition of claim 1, further comprising at least about 30 weight percent of ethanol.

3. The composition of claim 1 substantially free of silicones.

4. The composition of claim 1, wherein the combined amount of homosalate, octisalate, avobenzone, and octocrylene is at least about 21 weight percent based on the total weight of the composition.

5. The composition of claim 1 containing 10% by weight homosalate, 5% by weight octisalate, 3% by weight avobenzone, and 10% by weight octocrylene and no other oil soluble UV filters.

* * * * *

UNITED STATES PATENT AND TRADEMARK OFFICE
CERTIFICATE OF CORRECTION

PATENT NO. : 11,590,064 B2
APPLICATION NO. : 16/593035
DATED : February 28, 2023
INVENTOR(S) : Navya Mudya It is certified that error appears in the above-identified patent and that said Letters Patent is hereby corrected as shown below:

In the Specification

At Column 12, in Table 2 starting at Line 25, for Composition 3, Film Former Dermacryl 79 should read 1.75 for Weight % Film Former, and Film Former Lexfilm Sun should read 3.25 for Weight % Film Former. Corrected Table 2 should therefore read:

TABLE 2

| COMPOSITION | Film Formers | Weight % Film Former | Total Weight % Film Formers | SPF Value |
|---|---|---|---|---|
| 1 | Dermacryl 79 | 0.70 | 2.00 | 61.05 |
|   | Lexfilm Sun | 1.30 |      |       |
| A (Comparative) | Amphomer | 0.70 | 2.00 | 28.05 |
|   | Lexfilm Sun | 1.30 |      |       |
| B (Comparative) | Dermacryl 79 | 0.70 | 2.00 | 24.48 |
|   | Lexfilm Spray | 1.30 |      |       |
| C (Comparative) | Dermacryl 79 | 2.00 | 2.00 | 28.93 |
| D (Comparative) | Lexfilm Sun | 2.00 | 2.00 | 15.28 |
| 2 | Dermacryl 79 | 0.65 | 1.00 | 44.57 |
|   | Lexfilm Sun | 0.35 |      |       |
| 3 | Dermacryl 79 | 1.75 | 5.00 | 89.17 |
|   | Lexfilm Sun | 3.25 |      |       |
| 4 | Dermacryl 79 | 1.00 | 2.00 | 50.09 |
|   | Lexfilm Sun | 1.00 |      |       |
| 5 | Dermacryl 79 | 0.50 | 2.00 | 46.73 |
|   | Lexfilm Sun | 1.50 |      |       |

Signed and Sealed this
Twenty-first Day of October, 2025

John A. Squires
*Director of the United States Patent and Trademark Office*